US012788480B2

(12) United States Patent
Blanc

(10) Patent No.: US 12,788,480 B2
(45) Date of Patent: Nov. 10, 2026

(54) SYSTEMS AND METHODS FOR DISSECTING TISSUE

(71) Applicant: AB MEDICA, Centre Val de Loire (FR)

(72) Inventor: Alexandre Blanc, Centre Val de Loire (FR)

(73) Assignee: AB Medica, Centre Val de Loire (FR)

( * ) Notice: Subject to any disclaimer, the term of this patent is extended or adjusted under 35 U.S.C. 154(b) by 780 days.

(21) Appl. No.: 18/337,654

(22) Filed: Jun. 20, 2023

(65) Prior Publication Data

US 2023/0404654 A1 Dec. 21, 2023

Related U.S. Application Data

(60) Provisional application No. 63/354,179, filed on Jun. 21, 2022.

(51) Int. Cl.
*A61B 18/14* (2006.01)
*A61B 18/00* (2006.01)

(52) U.S. Cl.
CPC ...... *A61B 18/1482* (2013.01); *A61B 18/1445* (2013.01); *A61B 2018/00071* (2013.01)

(58) Field of Classification Search
CPC ............ A61B 18/1482; A61B 18/1445; A61B 2018/00071; A61B 2017/32035; A61B 2017/320044; A61B 17/3203
See application file for complete search history.

(56) References Cited

U.S. PATENT DOCUMENTS

| | | | | | |
|---|---|---|---|---|---|
| 5,022,414 | A * | 6/1991 | Muller | A61B 90/00 | 606/190 |
| 5,241,990 | A * | 9/1993 | Cook | A61M 1/772 | 604/32 |
| 5,449,356 | A * | 9/1995 | Walbrink | A61B 18/1482 | 606/49 |
| 5,514,091 | A * | 5/1996 | Yoon | A61F 13/38 | 600/207 |
| 5,591,183 | A * | 1/1997 | Chin | A61B 17/00008 | 606/167 |
| 5,871,462 | A * | 2/1999 | Yoder | A61B 17/1644 | 83/13 |
| 6,083,189 | A * | 7/2000 | Gonon | A61M 3/0216 | 604/118 |

(Continued)

*Primary Examiner* — Ryan J. Severson
(74) *Attorney, Agent, or Firm* — Farber LLC

(57) ABSTRACT

Systems and methods are provided for separating layers of tissue along planes by delivering a gas, such as $CO_2$, under pressure to the tissue. An instrument for dissecting tissue comprises an elongate shaft with a proximal end configured for coupling to an external source of gas and an open distal end fluidly coupled to the proximal end. An internal reservoir containing $CO_2$ under pressure is disposed within the instrument and a valve is coupled to the internal reservoir to open and close an outlet of the reservoir, thereby allowing the $CO_2$ from the internal reservoir to flow through the internal lumen and to a target site within the patient. The internal reservoir of gas allows the $CO_2$ to be delivered to the target site at a substantially higher flow rate, which increases the performance of the device in separating tissue layers.

24 Claims, 6 Drawing Sheets

(56) References Cited

U.S. PATENT DOCUMENTS

| | | | | | |
|---|---|---|---|---|---|
| 6,117,150 | A * | 9/2000 | Pingleton | A61B 90/00 604/35 |
| 6,190,381 | B1 * | 2/2001 | Olsen | A61B 18/1482 606/41 |
| 6,216,573 | B1 * | 4/2001 | Moutafis | A61B 17/3203 606/167 |
| 6,238,391 | B1 * | 5/2001 | Olsen | A61B 18/1206 604/35 |
| 9,615,847 | B2 * | 4/2017 | Kirkemo | A61B 1/32 |
| 10,172,637 | B2 * | 1/2019 | Caruso | A61B 17/3201 |
| 2015/0142039 | A1 * | 5/2015 | Kirkemo | A61B 1/32 606/185 |
| 2017/0209165 | A1 * | 7/2017 | Caruso | A61B 17/3203 |
| 2023/0404654 | A1 * | 12/2023 | Blanc | A61B 18/1482 |

* cited by examiner

SYSTEMS AND METHODS FOR DISSECTING TISSUE

BACKGROUND

The development of endoscopic procedures, such as laparoscopy, has led to a reduction in abdominal wall trauma and improved postoperative outcomes. These procedures, however, continue to be hindered by cumbersome and manually demanding instruments with well-known limitations, such as the fulcrum effect, haptic feedback and grasping force control. For example, in laparoscopic surgery, the lack of direct tissue palpation has significantly changed the haptic perception of surgeons. Thus, surgeons must plan their actions based on distorted haptic feedback perceived through instrument channels.

Further advances in laparoscopy require technological developments in tissue dissection to compensate for the surgeon's distancing from the operating field. For this reason, laparoscopic graspers, bipolar forceps, monopolar coagulation and powered instruments have all been developed. While these new instruments have advanced the field, their use for dissection of anatomic planes is limited. Tissue dissection requires the surgeon to get into the desired tissue plane in order to delineate structures, minimize bleeding and avoid visceral and vascular injury. The physical, mechanical and electrothermal properties of these devices, however, can cause plan fusion rather than division.

To overcome these drawbacks with tissue dissection in endoscopic procedures, pneumodissection instruments have been developed that deliver controlled bursts of high-pressure carbon dioxide ($CO_2$) through the distal end of an endoscopic instrument. These instruments have enabled surgeons to dissect along tissue planes without damaging the surrounding vessels or organs. $CO_2$ has emerged as a relatively safe gas for insufflation because it is non-flammable and extremely soluble.

While these pneumodissection devices have shown promise, they have not achieved widespread acceptance. One reason for this is that the delivery of $CO_2$ into the patient presents a risk of hypercarbia and pulmonary gas embolism (GE). The insufflation of $CO_2$ is rapidly absorbed into the circulatory system, while nitrogen and oxygen gases are slowly absorbed from the bloodstream, compounding the effects of GE when it occurs. The course of this complication can vary from asymptomatic up to impairment of normal flow through the right ventricle or pulmonary artery, potentially leading to acute heart failure.

Accordingly, it would be desirable to provide improved systems and methods for dissecting tissue planes during endoscopic surgical procedures, such as laparoscopy. In particular, it would be desirable to provide pneumodissection devices that substantially reduce, or eliminate, the risk of hypercarbia and GE, while still providing a sufficient velocity and/or volume of gas delivery to the target site to quickly and effectively dissect tissue planes during surgical procedures.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

Systems, devices and methods are provided for dissecting tissue, particularly for separating layers of tissue along planes by delivering a gas under pressure to the tissue. In one aspect, an instrument for dissecting tissue comprises an insert having an elongate shaft with a proximal end, an open distal end and an internal lumen fluidly coupling the proximal end to the open distal end. A handle is coupled to the elongate shaft and includes an internal lumen fluidly coupled to the internal lumen of the shaft and a proximal end configured for coupling to an external source of pressurized gas. An internal reservoir containing pressurized gas is disposed within the handle and a valve is coupled to the internal reservoir to open and close an outlet of the reservoir, thereby allowing the pressurized gas to flow through the internal lumen of the insert and to a target site within the patient.

The internal reservoir of pressurized gas provides an additional source of gas within the instrument for delivery to the target site. In addition, it allows for a larger volume of gas to be delivered to the target site within the patient more quickly (i.e., at a substantially higher flow rate) than would otherwise be the case if the gas were solely coming from the external gas source. This burst of gas is delivered in a shorter amount of time, thereby increasing the efficacy of the device in separating tissue layers.

Applicant has discovered that a certain volume of $CO_2$ can be delivered safely into a patient with minimal or no risk of hypercarbia and pulmonary gas embolism (GE). In particular, Applicant has shown in experimental studies that about 50 mL of $CO_2$ can be safely delivered into a patient in about 5 seconds with little or no risk of hypercarbia or GE. Applicant has also discovered that the speed at which the gas is delivered into the patient does not substantially impact the safety profile of the device so long as the total volume of gas is limited to 50 mL in five seconds. Thus, another advantage of this disclosed device is that a higher efficacy of dissection can be achieved within parameters that remain safe to the patient and minimize or eliminate any risk of hypercarbia or GE.

In certain embodiments, the gas within the internal reservoir is $CO_2$ under pressure of about 1 bar to about 10 bars, preferably under pressure of about 3-5 bars and more preferably about 3 bars. The internal reservoir is sized to contain about 1 mL to about 50 mL of the $CO_2$, preferably about 10 mL to about 30 mL. In embodiments, the gas is under sufficient pressure within the reservoir such that about 10 mL to 30 mL of $CO_2$ may be delivered through the open distal end of the shaft in about 1 second, preferably in about 0.5 seconds. This high velocity burst of $CO_2$ from the internal reservoir of the instrument provides optimal tissue dissection, particularly for separating tissue along planes.

The instrument may further comprise a user input, such as a trigger assembly, coupled to the handle and the valve. The trigger assembly may include an actuator, such as a push button or the like, that allows an operate to open the valve and release the gas from the internal reservoir. In certain embodiments, the actuator is biased into the closed position to ensure that the gas remains within the reservoir unless the operator actuators the trigger assembly.

The instrument may include a second trigger assembly to release the gas from the external gas source. Alternatively, a single trigger assembly can be configured to release gas from both the internal reservoir and the external source. In this latter embodiment, the internal gas is released rapidly from the instrument (e.g., up to 30 mL in about 0.5 to 1 seconds) and the external gas is then delivered following this initial burst.

In certain embodiments, the distal tip of the shaft comprises an electrically conductive material and the instrument further comprises an electrical connector on the handle configured for coupling to a source of electrical energy. The distal tip of the shaft may comprise a hook. In embodiments, the hook includes an internal lumen that is coupled to the internal reservoir of gas.

In another aspect, an instrument for dissecting tissue comprises an insert comprising an elongate shaft having a proximal end, an open distal end and an internal lumen fluidly coupling the proximal end to the open distal end. A handle is coupled to the elongate shaft and defines an internal lumen fluidly coupled to the internal lumen of the shaft and a proximal end configured for coupling to an external source of gas. The instrument further includes a flow regulator within the handle or the insert that is configured to regulate a flow rate of gas from the external source of gas through the internal lumen of the shaft.

The flow regulator provides the ability to set a consistent flow rate of the gas exiting the distal end of the instrument. This flow rate is preferably high enough to dissect tissue planes, while low enough to minimize or eliminate any risk of hypercarbia or GE. In an exemplary embodiment, the flow regulator is configured to provide a gas flow rate of about 9 mL/s to about 10 mL/s. Applicant has discovered that, with a maximum burst of 5 seconds, a flow rate greater than about 10 mL/s may present risks of GE, while a flow rate less than about 9 mL/s may compromise performance of the instrument.

In embodiments, the flow regulator comprises a main body with an internal lumen having a proximal end fluidly coupled to the internal lumen of the handle and an open distal end. The main body of the flow regulator comprises a substantially cylindrical body with an outer surface and one or more grooves formed in the outer surface. The grooves fluidly couple the open distal end of the main body with one or more fluid outlets in the instrument. The fluid outlets, in turn, are coupled to the internal lumen of the insert.

The grooves in the main body of the flow regulator establish a reduced-area flow path for the gas to limit the gas flow rate at the distal tip of the instrument. The grooves are preferably sized and shaped to regulate the gas flow rate therethrough to about 1 mL/s to about 20 mL/s. In certain embodiments, the annular tube comprises at least two grooves circumferentially spaced from each other around the outer surface of the annular tube. In other embodiments, the tube comprises at least three grooves.

In another aspect, method for dissecting tissue in a patient comprises coupling a proximal end of an instrument to an external source of gas, positioning a distal tip of the instrument adjacent to, or near, a target site on, or within, the patient, and releasing gas from a reservoir in a handle of the instrument such that the gas flows through an internal lumen of the instrument and through the distal tip.

In certain embodiments, the gas within the internal reservoir is $CO_2$ under pressure of about 1 bar to about 10 bars, preferably under pressure of about 3-5 bars. The internal reservoir is sized to contain about 1 mL to about 50 mL of the $CO_2$, preferably about 10 mL to about 30 mL. In embodiments, the gas is under sufficient pressure within the reservoir such that about 10 mL to about 30 mL is delivered through the open distal end of the shaft in about 1 second, preferably about 0.5 seconds.

In embodiments, the method further comprises releasing gas from the external source of gas through the internal lumen and through the distal tip of the instrument. The gas flow rate may be regulated with an internal flow regulator within the handle or insert. The flow rate may be between about 1 mL/s to about 20 mL/s.

The method may further comprise regulating the flow rate of the external source of gas with a flow regulator housed within the insert or the handle of the instrument. The flow regulator preferably maintains the external gas flow rate at about 9 mL/s to about 10 mL/s.

BRIEF DESCRIPTION OF THE DRAWINGS

The accompanying drawings, which are incorporated in and constitute a part of this description, illustrate several embodiments and together with the description, serve to explain the principles of the devices and methods disclosed herein.

DETAILED DESCRIPTION

Particular embodiments are described hereinbelow with reference to the accompanying drawings; however, it is to be understood that the disclosed embodiments are merely exemplary and that the devices and methods disclosed herein may be embodied in various forms. Therefore, specific structural and functional details disclosed herein are not to be interpreted as limiting, but merely as a basis for the claims and as a representative basis for teaching one skilled in the art to variously employ virtually any appropriately detailed structure. Well-known functions or constructions are not described in detail to avoid obscuring the description in any unnecessary detail. It should be understood also that the drawings are not drawn to scale and are not intended to represent absolute dimensions or relative size. Instead, the drawings help to illustrate the concepts described herein.

Systems, devices and methods are provided for dissecting tissue, particularly for separating layers of tissue along planes by delivering a gas, such as $CO_2$, under pressure to the tissue. The devices described herein may also include an electrosurgical element for heating, ablating, cauterizing, or dissecting tissue in combination with the delivery of gas under pressure. The devices described herein are particularly useful for separating layers of tissue in endoscopic procedures, such as cholecystectomies, nephrectomies, cystic pedicle dissections, hepatic pedicle dissections, tumor resection procedures and the like.

Figure 1:
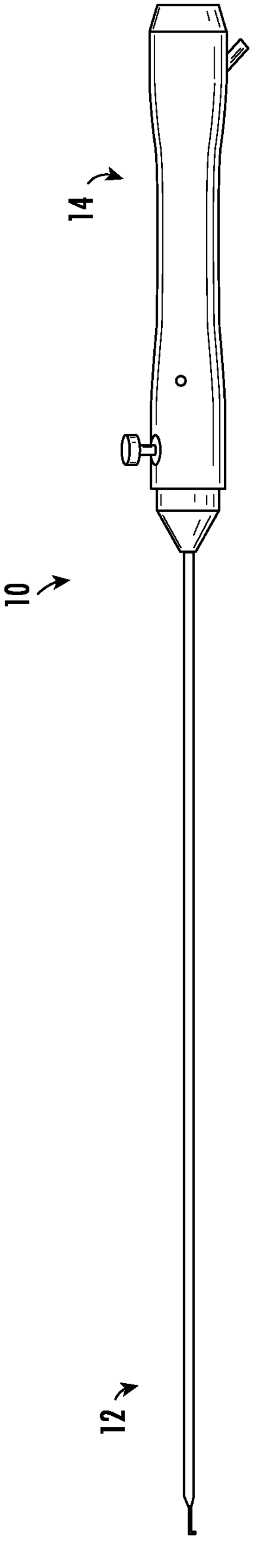
FIG. 1 is a side view of an instrument for dissecting tissue with a gas.
Figure 2:
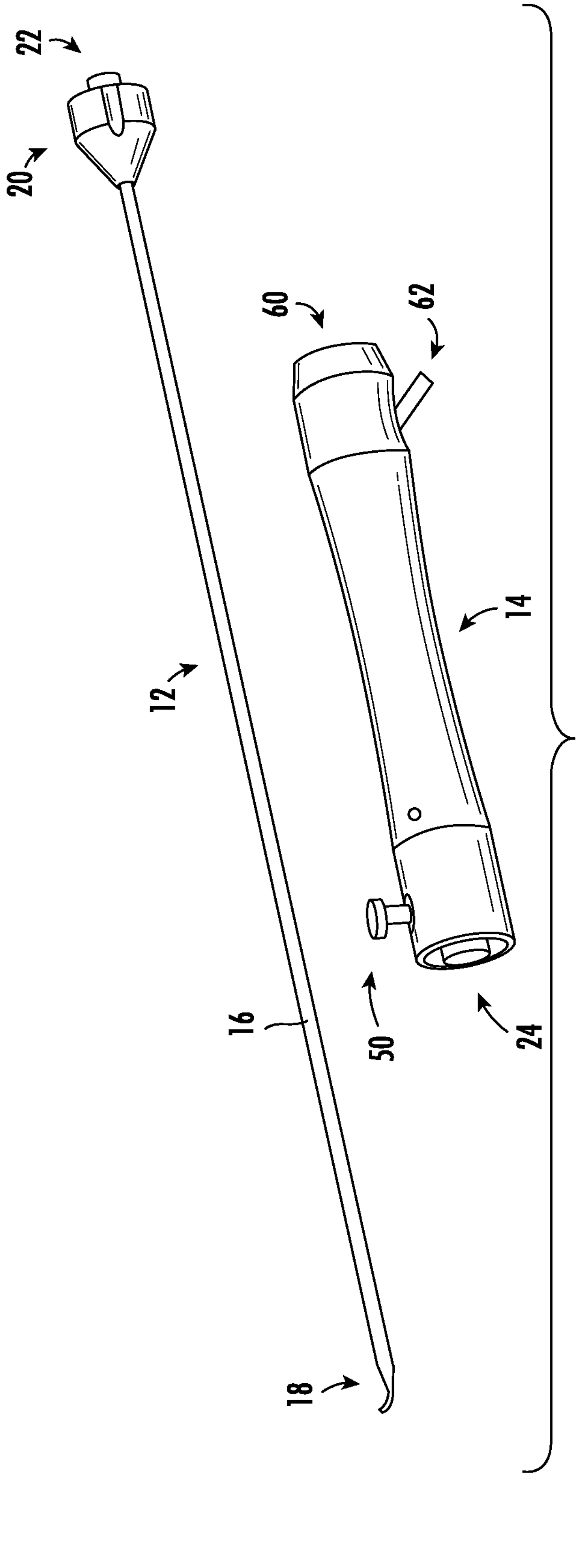
FIG. 2 is an exploded view of a handle and an insert of the instrument of FIG. 1.
Figure 3:
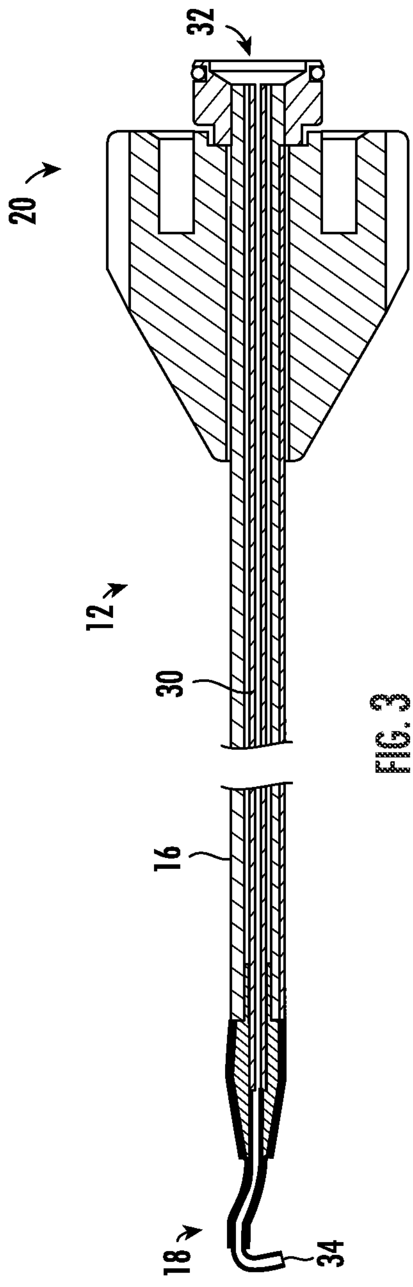
FIG. 3 is a cross-sectional view of the instrument of FIG. 1.

Referring now to FIGS. 1 and 2, an instrument 10 for dissecting tissue comprises an insert 12 coupled to a handle 14. Insert 12 includes an elongate shaft 16 with a distal tip 18 and a proximal flange 20. Flange 20 has a mating feature 22, such as a screw, nut, interlocking member, press-fit member, or the like for removably coupling insert 12 to a corresponding mating feature 24 on handle 14. Alternatively, insert 12 and handle may be formed as a single unitary component. As shown in FIG. 3, insert 12 includes an internal lumen 30 extending from a proximal opening 32 to a distal opening 34 on tip 18 for allowing the passage of a fluid, such as a gas, therethrough. Tip 18 may comprise an electrically conductive material, such as stainless steel or the like, for applying electrical energy to tissue (discussed below).

Figure 4:
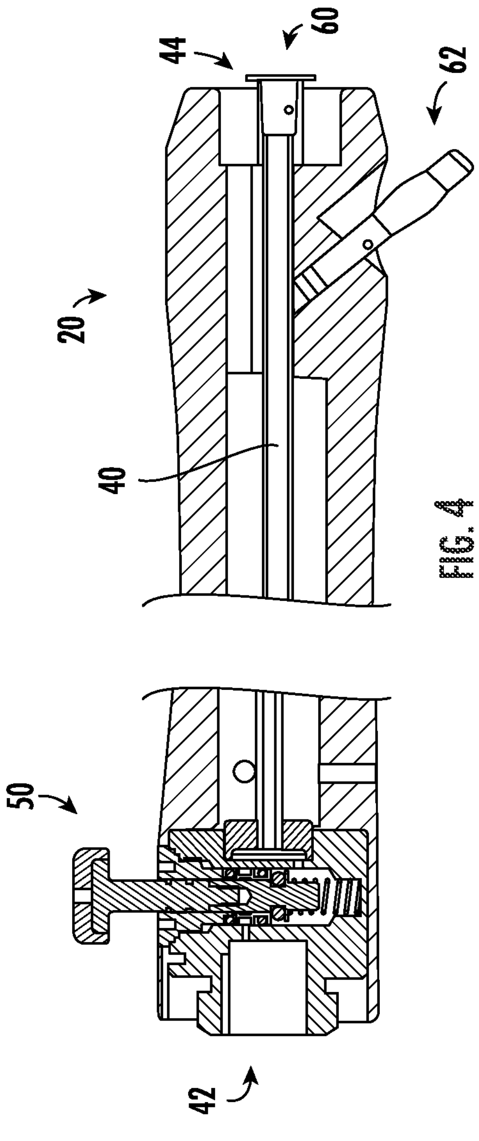
FIG. 4 is a cross-sectional view of the handle of FIG. 2.
Figure 7:
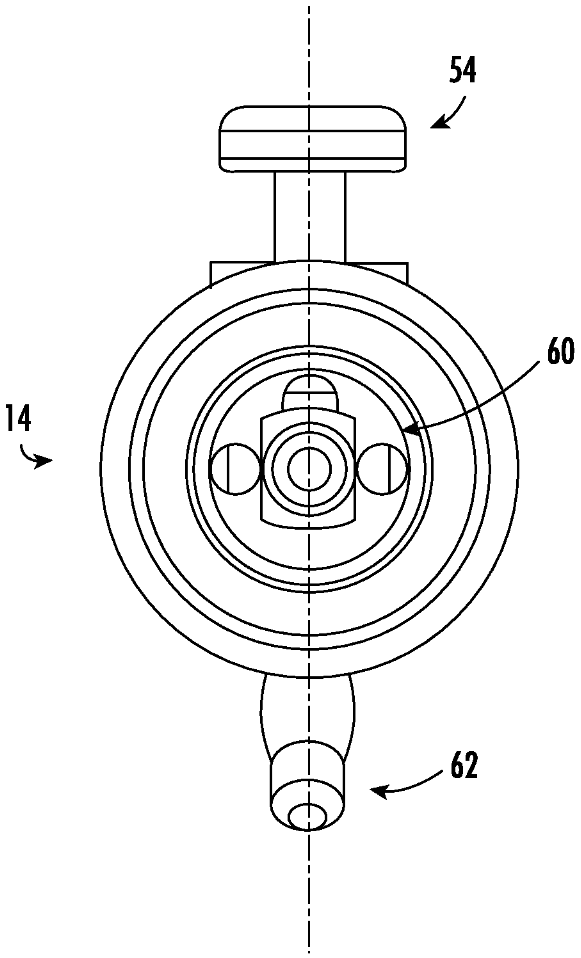
FIG. 7 is a cross-sectional view of the handle of FIG. 2 taken along the longitudinal axis of the instrument.

As shown in FIGS. 2 and 4, handle 20 includes an internal lumen 40 having a distal opening 42 configured for alignment with proximal opening 32 of insert 12 and a proximal opening 44 having a coupling element 60 configured for coupling to an external source of fluid or gas, such as $CO_2$ (see also FIG. 7). Coupling element 60 may, for example, comprise a LUER lock, or other suitable device that is designed to secure to flexible tubing. The flexible tubing may, in turn, be coupled to one or more pressure regulators for a source of external gas, such as a standard $CO_2$ cylinder that can be found in most hospitals.

Handle 20 also includes an electrical connector 62 configured for coupling to a source of electrical energy, such as a monopolar or bipolar current generator. Electrical connector 62 is coupled to distal tip 18 through a wire or other suitable connector (not shown). In this embodiment, insert 12 and handle 14 preferably comprise an insulating material, such as plastic, polymers or the like, to ensure that electric current flowing through instrument 10 remains confined to the connecting wires.

Figure 5:
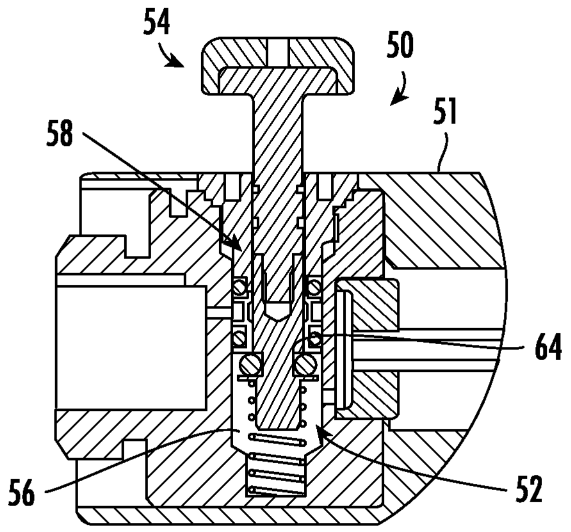
FIG. 5 is an enlarged view of a cross-section of one portion of the handle.

Handle 20 further includes a trigger assembly 50 for actuating the flow of gas from the external source through the internal lumens of handle 14 and insert 12. As shown in FIG. 5, trigger assembly 50 may comprise an actuator 54, such as a push button or the like, extending through an outer surface 51 of handle 20 that allows a user to push trigger 50 into handle 14 to release the flow of gas through instrument 10. In certain embodiments, trigger assembly 50 further comprises a jack 52 or the like, comprising a chamber 56 and an outlet 58 within chamber 56, and a coupling element for connecting the outlet made in the chamber with the outlet port 11 made on the handle. For example, coupling element may include an outlet duct in which is mounted a non-return valve or the like.

Of course, instrument 10 may use other triggers or actuators for releasing gas through instrument, such as hydraulic, electric, pneumatic, piezoelectric, release valves, ball valves, diaphragm valves, needle valves, butterfly valves, or the like. In addition, the user input device may comprise a rotatable knobs, a linear slide or any other type of user input to actuator the flow of gas through the instrument.

Figure 6:
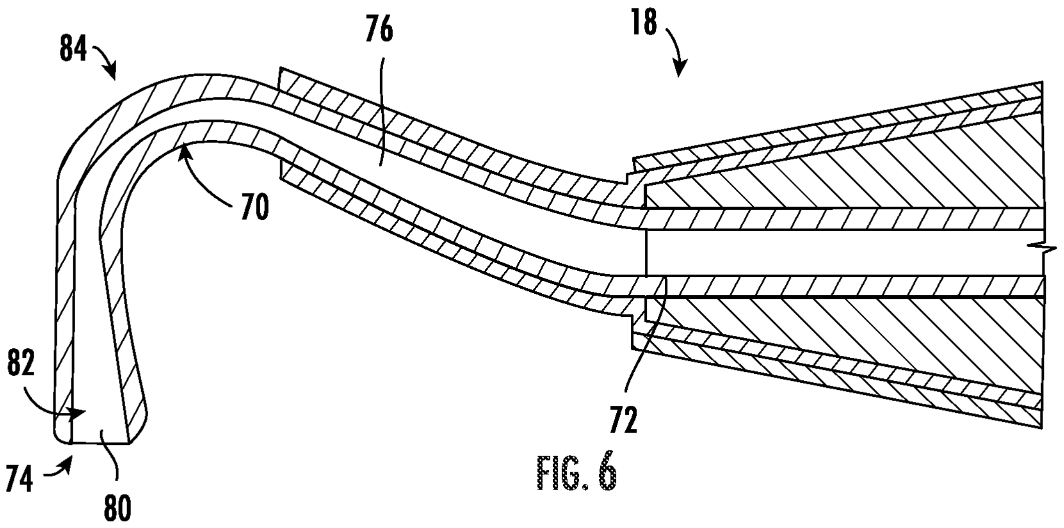
FIG. 6 is a cross-sectional view of one embodiment of a distal tip of the insert.

Referring now to FIG. 6, distal tip 18 of insert 12 further includes a tube 70 defined between a proximal end 72 and a distal end 74 and comprising, over its entire length and along its longitudinal axis, a through hole 76 defined between a proximal inlet 78 and a distal outlet 80. In one embodiment, the distal portion of through-hole 76 is flared substantially in a truncated cone 82, optionally of revolution, the large base of this truncated cone being substantially in the plane of the distal outlet 80 of the through hole 76. In an exemplary embodiment, one portion of the tube 70 is shaped as a hook 84. This hook 84 comprises a curved part followed by a substantially rectilinear part that comprises the distal end 74. The through-hole portion flared into a truncated cone is produced in the substantially rectilinear part of the hook 84, the small base of the truncated cone being substantially situated in the plane which separates the parts of the hook curved and rectilinear respectively. A more complete description of one embodiment of distal end 18 can be found in French Patent Application No. 3104019, the complete disclosure of which is incorporated herein by reference for all purposes.

While a hook 84 with a truncated cone has been described above, the devices and methods disclosed herein are not limited to this embodiment. For example, distal tip 18 may comprise a hook-shaped device that does not include a truncated cone, but instead has substantially parallel internal walls, or one that defines other shapes, such as triangular or the like. In addition, distal tip 18 may be substantially straight, or it may have a curve that is not as pronounced as the hook 84 shown in FIG. 6.

In certain embodiments, the maximum inlet pressure of hook 84 is about 7500 mmHG, preferably between about 750 mmHg and about 2250 mmHg depending on the desired flow rate through hook 84. For example, gas flow rates of about 5 mL/s can be obtained with an inlet pressure of about 750 mmHg. Gas flow rates of about 10 mL/s can be obtained with an inlet pressure of about 1125 and 1500 mmHg and gas flow rates of about 15 mL/s can be obtained with an inlet pressure of about 1875 to about 2250 mmHg.

Applicant has discovered that a certain volume of gas, such as $CO_2$, can be delivered safely into a patient with minimal or no risk of hypercarbia and pulmonary gas embolism (GE). In particular, Applicant has shown in experimental studies that about 50 mL of $CO_2$ can be safely delivered into a patient in about 5 seconds with little or no risk of hypercarbia or GE. These experiments have been recently published as of Dec. 6, 2021 in Surgical Endoscopy titled "New 5-mm laparoscopic pneumodissector device to improve laparoscopic dissection: an experimental study of its safety in a swine model", authored by Theophile Guilbaud, Alexia Cermolacce, Stephane Berdah and David Jeremie Birnbaum, the complete disclosure of which is incorporated herein by reference for all purposes as if copied and pasted herein.

In this experiment, Applicant assessed the safety of a burst of high pressure $CO_2$ using a mm laparoscopic pneumodissector (PD) similar to the devices described herein. The PD was operated at different flow rates and for different operating times to assess the risk of gas embolism (GE) in a swine model. In a first step, the PD was placed 10 mm deep into the liver of the swine and the PD was directly introduced into the lumen of the inferior vena cava. Different flow rates of 5, 10 and 15 mL/s were used. In a second step, the PD was used during a laparoscopic dissection task (cystic and hepatic pedicles dissection, cholecystectomy and right nephrectomy) in comparison with the use of a standard electrosurgical hook device (the control group).

Applicant discovered that no severe or fatal GE occurred when a burst of high-pressure $CO_2$ was applied with 3 or 5 seconds with PD flow rates of 5 and 10 mL/s. The use of the PD did not increase operative time or blood loss. The quality of the dissection was significantly improved compared to the control group. Accordingly, Applicant has established that the PD device described herein appears to be free from GE risk when consecutive bursts of high-pressure $CO_2$ are delivered for 3-5 seconds with a flow rate of 10 mL/s, or up to about 50 mL/s within 5 seconds.

Figure 8:
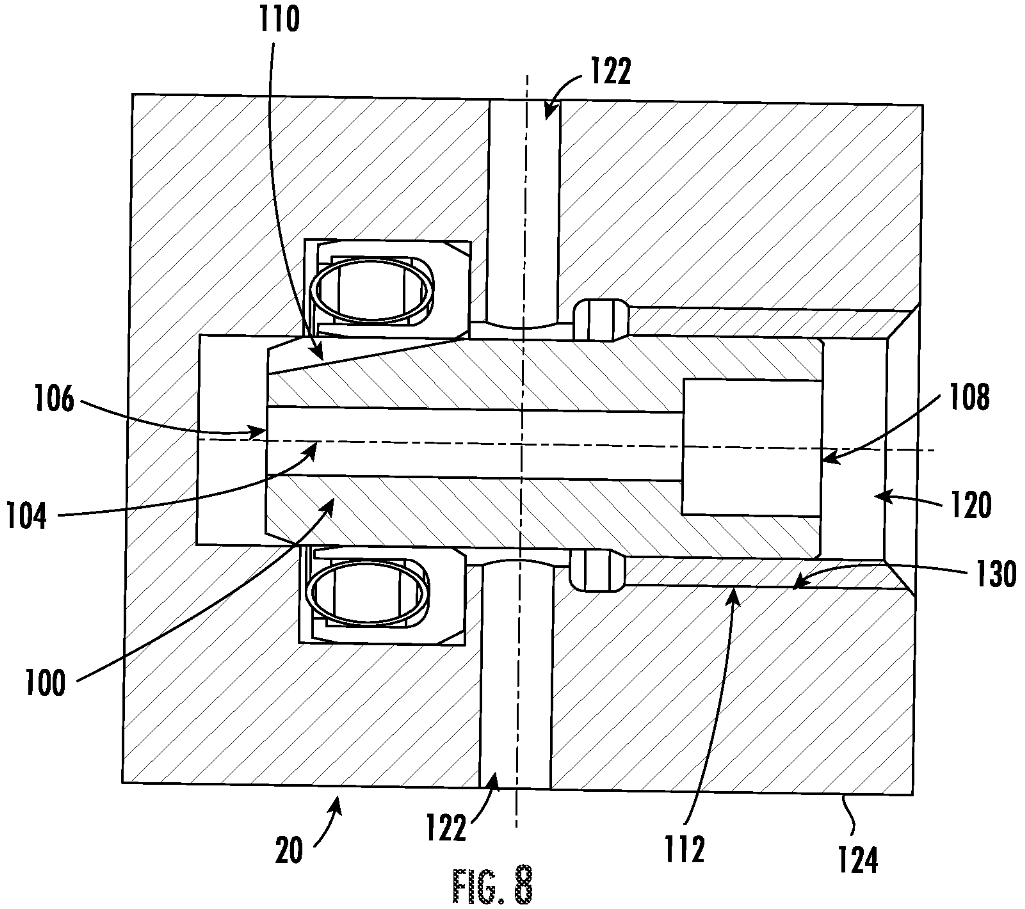
FIG. 8 is a perspective view of a flow regulator for an embodiment of the instrument of FIG. 1.
Figure 9:
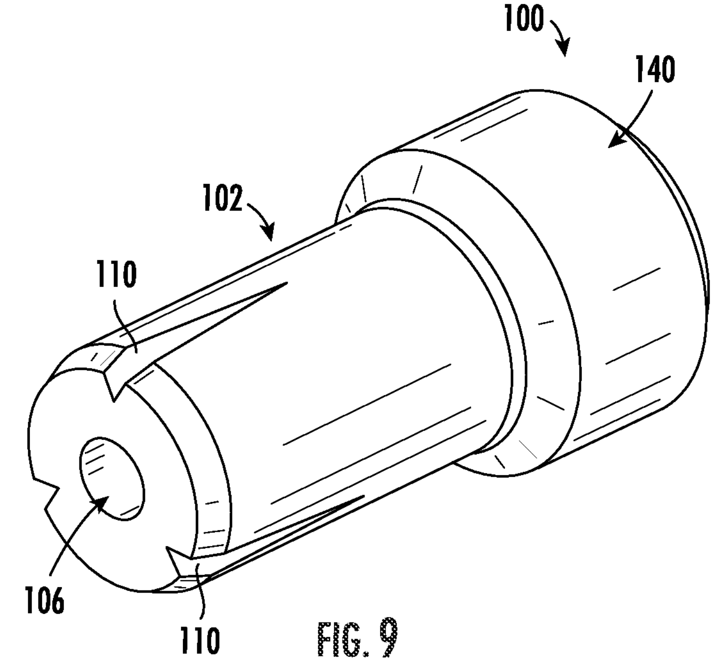
FIG. 9 is a cross-sectional view of the insert of the instrument incorporating the flow regulator of FIG. 8.

Referring now to FIGS. 8 and 9, instrument 10 may include an internal flow regulator 100 for regulating or limiting the flow rate of gases from the external gas source (and/or the internal reservoir 210 discussed below) through internal lumens 30 and 40. Flow regulator 100 may be housed within insert 12 or handle 14. In one embodiment, flow regulator 100 is housed within proximal flange 20 of insert 12.

Flow regulator 100 comprises a substantially cylindrical main body 102 having an internal passage or lumen 104 extending through main body 102. Internal passage 104 includes open distal and proximal ends 106, 108, Proximal end 108 is aligned with one of the internal lumens in insert 12 or handle 14 such that gas flows through lumen 104. Flow regulator 100 further includes one or more grooves 110 within an outer surface 112 of main body 102. In certain embodiments, flow regulator 100 includes two or more grooves 110. In an exemplary embodiment, flow regulator 100 includes three grooves 110 circumferentially spaced from each other around outer surface 112. Grooves 110 may be spaced at angles of about 120 degrees from each other around outer surface 112.

Proximal flange 20 of insert 12 includes a chamber 120 for housing flow regulator 100 and one or more lateral passages 122 extending from chamber 120. Lateral passages 122 may be fluidly coupled to internal lumen 30 within insert 12 such that gas exiting distal end 106 of flow regulator 100 flows through grooves 110 and passages 122 to the distal tip 18 of instrument 100. Flow regulator 100 is preferably sized such that outer surface 112 is in contact with an inner surface 130 of chamber 120. This ensures that gas does not flow around flow regulator 110 into chamber 120. Flow regulator 110 may include a proximal flange 140 designed to seat within an enlarged proximal portion of chamber 120 to secure flow regulator 110 in position within flange 20.

Grooves 110 are preferably sized and shaped to set a consistent flow rate of the gas exiting the distal end of the instrument. This flow rate is preferably high enough to dissect tissue planes, while low enough to minimize or eliminate any risk of hypercarbia or GE. In an exemplary embodiment, the flow regulator is configured to provide a gas flow rate of about 9 mL/s to about 10 mL/s. As discussed above, applicant has discovered that, with a maximum burst of 5 seconds, a flow rate greater than about 10 mL/s may present risks of GE, while a flow rate less than about 9 mL/s may compromise performance of the instrument.

Figure 10:
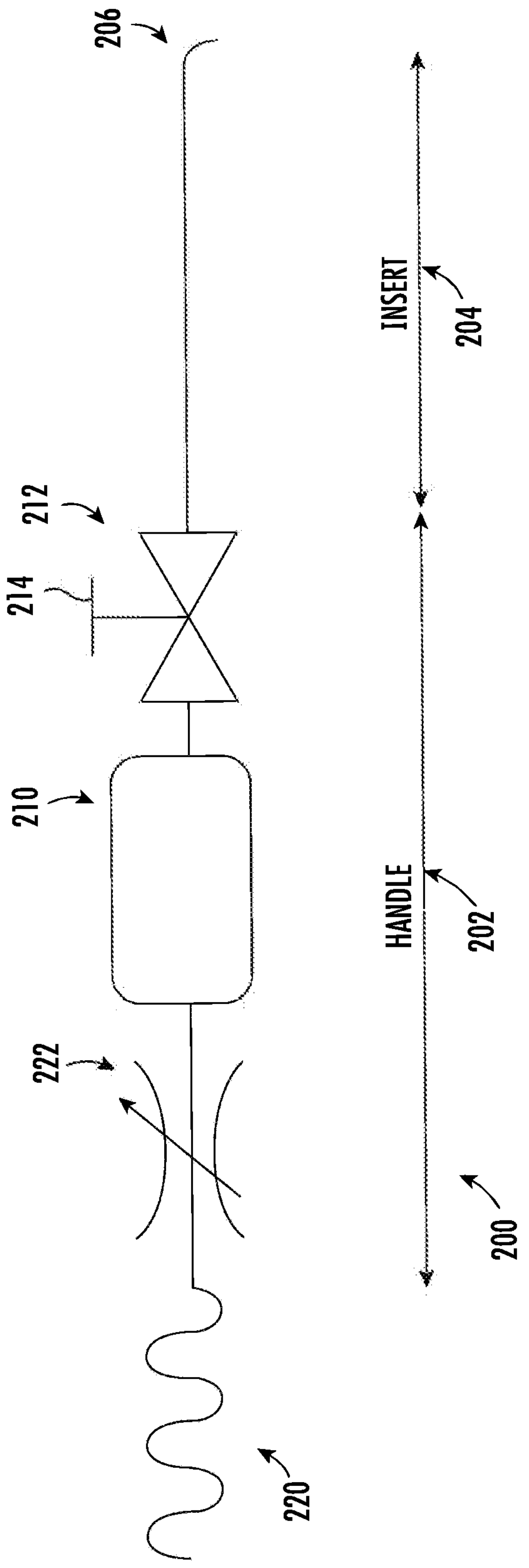
FIG. 10 is a schematic of an embodiment of an instrument for dissecting tissue with a gas.

Referring now to FIG. 10, another embodiment of an instrument 200 for dissecting tissue in a human body will now be described. As shown, instrument 200 includes a handle 202 and an insert 204. Handle 202 includes an internal lumen (not shown) with a proximal end (not shown) configured for coupling to an external source of gas 220, and a distal end fluidly coupled to an internal lumen (not shown) within insert 204. Internal lumen of insert 204 comprises a distal opening 206 for delivering the gas therethrough. Handle 202 and insert 204 are only shown schematically in FIG. 10 and may have a similar construction as handle 14 and insert 12 described above, or they may be constructed according to other known devices in the art.

In this embodiment, instrument 200 includes a gas reservoir 210 within handle 202 and a flow regulator or valve 222 disposed within handle 202, insert 204 or therebetween. Gas reservoir 210 is configured to hold a gas, such as $CO_2$, under pressure therein.

Internal reservoir 210 provides an additional source of gas within instrument 200 for delivery to the target site. In addition, it allows for a larger volume of gas to be delivered to the target site within the patient more quickly (i.e., at a substantially higher flow rate) than would otherwise be the case if the gas were solely coming from the external gas source. This increases the flow at the beginning of the burst, which reduces the delay and improves the efficacy of the device in separating tissue layers.

Applicant has discovered that the speed at which the volume of $CO_2$ is delivered into the patient does not substantially impact the safety profile of the device so long as the total volume of $CO_2$ is limited to 50 mL in five seconds. Thus, another advantage of this disclosed device is that a higher efficacy of dissection can be achieved within parameters that remain safe to the patient and minimize or eliminate any risk of hypercarbia or GE.

In certain embodiments, the gas within the internal reservoir is $CO_2$ under pressure of about 1 bar to about 10 bars, preferably under pressure of about 8 bars. The internal reservoir is sized to contain about 1 mL to about 50 mL of the $CO_2$, preferably about 10 mL to about 30 mL. In embodiments, the gas is under sufficient pressure within the reservoir such that about 10 mL to 30 mL of $CO_2$ may be delivered through the open distal end of the shaft in about 1 second, preferably in about 0.5 seconds. This high velocity burst of $CO_2$ from the internal reservoir of the instrument provides optimal tissue dissection, particularly for separating tissue along planes.

Valve 212 is coupled to either the internal lumen within handle 202 or the internal lumen with insert 204 and may be used to control fluid flow from both reservoir 210 and the external source of gas 220. Alternatively, valve 212 may be coupled to an outlet (not shown) of reservoir 210 that is suitably coupled to one of these internal lumens. In this embodiment, valve 212 may be used to control gas flow from reservoir 210 only, and instrument 200 will include another valve or trigger mechanism for controlling flow from external gas source 220.

Valve 212 includes an actuator 214 for opening and closing of valve 212 and may comprise any suitable valve known to those in the art, such as ball, diaphragm, needle, butterfly, plug, piston, pinch, gate, globe or the like. In one embodiment, valve 212 and actuator 214 have a similar construction to trigger assembly 50 described above.

In use, a physician or other operator may connect an external regulator to a $CO_2$ cylinder and then connect the one end of a flexible tube to the regulator and the other end to the LUER connection on the proximal end of handle 202. The $CO_2$ cylinder is opened until the pressure reaches a suitable level, e.g., about 3-5 bars, preferably about 3 bars. Insert 204 may then be coupled to handle 202, as discussed above. Alternatively, insert 204 and handle 202 may be formed from a single unitary component. In certain embodiments, handle 202 may also be connected to a suitable electrosurgical power source, such as a monopolar cable, as discussed above.

The physician then advances distal tip 206 of instrument 200 to a target location on a patient's body. The physician may then open valve 212 with actuator 214 by, for example, pushing down on a suitable trigger mechanism. Opening valve 212 causes the gas in reservoir 210 to be released, such that it flows through the internal lumens of handle 202 and insert 204 through distal tip 206 to the target site. At the same time, gas flows from the external gas source 220 through the same internal lumens to the target site.

Since the gas within reservoir 210 is under pressure, it will be substantially entirely released through distal tip 206 at a rate that depends upon the pressure. In the preferred embodiments, this pressure is sufficient to release substantially all of the gas within reservoir and through distal tip in about 1 second, preferably in about 0.5 seconds. This provides a much higher flow rate of gas through distal tip 206 than would otherwise be provided from external gas source 200. This higher flow rate provides improves performance of tissue dissection.

Instrument 200 may include a flow regulator (not shown) for regulating the flow rate of gas from external gas source 220 through instrument 200 to distal tip 206. The flow regulator may be similar in construction to flow regulator 110 discussed above, or it may have a different construction. In certain embodiments, the gas flow from reservoir 210 may be sufficient to provide tissue separation (i.e., 30 mL of gas delivered at 0.5 seconds). In these embodiments, flow regulator 222 will be closed or set to 4 mL/s. In other embodiments, additional gas flow from external gas source 220 may be desired. In such instances, regulator 222 may be set to a suitable gas flow rate of, for example, about 1 mL/s to about 15 mL/s, preferably 4 mL/s.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the description. Accordingly, the description is intended to embrace all such alternatives, modifications, and variances. As well, one skilled in the art will appreciate further features and advantages based on the above-described embodiments. Accordingly, this description is not to be limited by what has been particularly shown and described, except as indicated by the appended claims.

What is claimed is:

1. An instrument for dissecting tissue, the instrument comprising:

an elongate shaft with an internal lumen having a proximal end configured for coupling to an external source of gas and an open distal end;

an internal reservoir within the shaft, the reservoir containing gas under pressure and having an outlet fluidly coupled to the internal lumen; and a valve coupled to the outlet for opening and closing the outlet.

2. The instrument of claim 1, further comprising:

an insert comprising an elongate shaft with a proximal end, an open distal end and an internal lumen fluidly coupling the proximal end to the open distal end; and a handle coupled to the elongate shaft and defining an internal lumen fluidly coupled to the internal lumen of the shaft and having a proximal end configured for coupling to an external source of gas.

3. The instrument of claim 2, wherein the internal reservoir resides in the handle.

4. The instrument of claim 1, wherein the gas is carbon dioxide ($CO_2$) under pressure of about 1 bar to about 10 bars.

5. The instrument of claim 4, wherein the $CO_2$ is under pressure of about 3 bars.

6. The instrument of claim 4, wherein the internal reservoir contains about 1 mL to about 50 mL of the $CO_2$.

7. The instrument of claim 4, wherein the internal reservoir contains about 10 mL to about 30 mL of the $CO_2$ under sufficient pressure for delivery through the open distal end of the shaft in about 1 second.

8. The instrument of claim 7, wherein the $CO_2$ is delivered through the open distal end of the shaft in about 0.5 seconds.

9. The instrument of claim 1, further comprising a flow regulator configured to regulate a flow rate of gas from the external source of gas through the internal lumen of the shaft.

10. The instrument of claim 9, wherein the flow regulator comprises a main body with an internal lumen having a proximal end fluidly coupled to the internal lumen and an open distal end.

11. The instrument of claim 10, wherein the main body of the flow regulator comprises an annular tube with an outer surface and one or more grooves in the outer surface, wherein the one or more grooves fluidly couple the distal end of the main body with one or more fluid outlets within the instrument.

12. The instrument of claim 11, wherein the one or more fluid outlets are coupled to the internal lumen within the shaft.

13. The instrument of claim 9, wherein the flow regulator is configured to provide a gas flow rate of about 1 mL/s to about 15 mL/s through the open distal end of the insert.

14. The instrument of claim 1, further comprising a trigger coupled to the shaft and the valve, wherein the trigger is configured to open and close the valve.

15. The instrument of claim 1, wherein the distal tip of the shaft comprises an electrically conductive material, the instrument further comprising an electrical connector configured for coupling to a source of electrical energy.

16. The instrument of claim 1, wherein the distal tip of the shaft comprises a hook.

17. A method for dissecting tissue in a patient, the method comprising:

coupling a proximal end of an instrument to an external source of gas;

positioning a distal tip of the instrument adjacent to, or near, a target site on, or within, the patient; and releasing gas from a reservoir in a handle of the instrument such that the gas flows through an internal lumen of the instrument and through the distal tip.

18. The method of claim 17, wherein the gas is carbon dioxide (CO2) under pressure of about 1 bar to about 10 bars.

19. The method of claim 18, wherein the $CO_2$ is under pressure of about 3 bars.

20. The method of claim 17, wherein the internal reservoir contains about 1 mL to about 50 mL of the $CO_2$.

21. The method of claim 20, further comprising releasing about 1 mL to about 50 mL of the $CO_2$ through the distal tip in about 1 second.

22. The method of claim 17, further comprising releasing gas from the external source of gas through the internal lumen and through the distal tip of the instrument.

23. The method of claim 22, further comprising regulating a flow rate of the gas.

24. The method of claim 23, wherein the flow rate is between about 1 mL/s and about 15 mL/s.

* * * * *